United States Patent
Cheng et al.

(10) Patent No.: US 12,011,472 B2
(45) Date of Patent: Jun. 18, 2024

(54) USE OF RAMIE EXTRACT IN PREPARING A COMPOSITION FOR IMPROVING THE ACTIVITY OF MITOCHONDRIA AND IMPROVING THE ACTIVITY OF TELOMERASE

(71) Applicant: TAIWAN MITOCHONDRION APPLIED TECHNOLOGY CO., LTD., Zhubei (TW)

(72) Inventors: Han-Chung Cheng, Zhubei (TW); Shun-Chieh Yang, Zhubei (TW); An-Ling Cheng, Zhubei (TW)

(73) Assignee: TAIWAN MITOCHONDRION APPLIED TECHNOLOGY CO., LTD., Zhubei (TW)

( * ) Notice: Subject to any disclaimer, the term of this patent is extended or adjusted under 35 U.S.C. 154(b) by 0 days.

(21) Appl. No.: 17/831,063

(22) Filed: Jun. 2, 2022

(65) Prior Publication Data

US 2023/0081868 A1    Mar. 16, 2023

(30) Foreign Application Priority Data

Aug. 27, 2021 (CN) .......................... 202110996801.8

(51) Int. Cl.
| | | |
|---|---|---|
| *A61K 36/185* | (2006.01) | |
| *A61K 31/192* | (2006.01) | |
| *A61P 3/00* | (2006.01) | |

(52) U.S. Cl.
CPC .......... *A61K 36/185* (2013.01); *A61K 31/192* (2013.01); *A61P 3/00* (2018.01); *A61K 2236/15* (2013.01); *A61K 2236/331* (2013.01)

(58) Field of Classification Search
None
See application file for complete search history.

(56) References Cited

PUBLICATIONS

Wang et al. (2018) Industrial Crops and Products, 122: 430-437. (Year: 2018).*
Prasad et al. (2017) Mechanisms of Ageing and Development 164; 61-66. (Year: 2017).*
Lee et al. (2014) J. Korean Soc. Appl. Biol. Chem. 57(5): 639-645. (Year: 2014).*
Lee et al.(2016) Asian Australas J. Anim. Sci. vol. 29, No. 9, 1338-1344. (Year: 2016).*
Chen et al. (2014) PLoS ONE 9(9): 9 pages. (Year: 2014).*

* cited by examiner

*Primary Examiner* — Russell G Fiebig
(74) *Attorney, Agent, or Firm* — Maschoff Brennan

(57) ABSTRACT

A use of a ramie extract in preparing a composition for anti-aging is provided. The composition containing ramie extract can improve the function and activity of mitochondria and telomerase and protect mitochondria from oxidative stress, including decrease in the proton leakage, increase in the ATP production, increase in the spare respiratory capacity, increase in the maximal respiratory capacity, or increase in the ATP coupling efficiency.

5 Claims, 7 Drawing Sheets

USE OF RAMIE EXTRACT IN PREPARING A COMPOSITION FOR IMPROVING THE ACTIVITY OF MITOCHONDRIA AND IMPROVING THE ACTIVITY OF TELOMERASE

CROSS-REFERENCE TO RELATED APPLICATIONS

This non-provisional application claims priority under 35 U.S.C. § 119(a) on Patent Application No. 202110996801.8 filed in China on Aug. 27, 2021, the entire contents of which are hereby incorporated by reference.

BACKGROUND

1. Technical Field

The present disclosure relates to the use of ramie extract in preparing a composition for anti-aging.

2. Related Art

Mitochondria (called "mitochondrion" in singular form) are places where oxidative phosphorylation (OXPHOS) and adenosine triphosphate (ATP) synthesis occur. Since ATP is used as a source of energy in a cell, the mitochondria are described as the powerhouse of the cell. In addition to generate energy required by the cell, the mitochondria also participate in cell division, cell signaling and apoptosis of the cell, and the mitochondria has the ability to control the cell-division cycle. Therefore, the mitochondria are considered to be closely related to the aging of organisms.

Telomere is a region of repetitive nucleotide sequences at the terminal region of chromosomal DNA of eukaryotes and functions to ensure the integrity of chromosomes and control the cell-division cycle. Due to the limitation in the DNA replication mechanism, the telomere at the terminal region of chromosomes cannot be completely replicated when replicating. Once the telomere is shortened to depleted, the cell will trigger apoptosis and go dead.

Telomerase is a complex composed of RNA and protein, and it can repair and elongate telomeres so that the loss of telomeres due to cell division is reduced. Telomerase with high activity is usually detected in hematopoietic cells, stem cells, and germ cells. Therefore, telomerase is considered to be closely related to the aging of organisms.

Both mitochondria and telomeres are related to the aging of cells, even organisms. Therefore, how to protect and repair mitochondria to maintain the activity thereof and reduce the collapse thereof and how to increase the activity of telomerase to reduce the speed of the loss of telomeres become important issues for anti-aging.

SUMMARY

Accordingly, the present disclosure provides a use of a ramie extract for increasing the activity of mitochondria and a use of a ramie extract for increasing the activity of telomerase, for the purpose of anti-aging.

According to one embodiment of the present disclosure, a use of a ramie extract in preparing a composition for improving the activity of mitochondria is provided.

According to one embodiment of the present disclosure, a use of a ramie extract in preparing a composition for improving the activity of telomerase is provided.

In view of the above description, according to the present disclosure, referring to the use of ramie extract in preparing a composition for anti-aging, mitochondria are protected from oxidative stress to maintain their function and activity, including decrease in the proton leakage, increase in the ATP production, increase in the spare respiratory capacity, increase in the maximal respiratory capacity, increase in the ATP coupling efficiency, or increase in Bioenergetic Health Index (BHI), for the purpose of anti-aging. According to the present disclosure, referring to the use of ramie extract in preparing a composition for anti-aging, the activity of telomerase is also increased to repair telomere and reduce the speed of the loss of telomeres for the purpose of anti-aging.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

Figure 1:
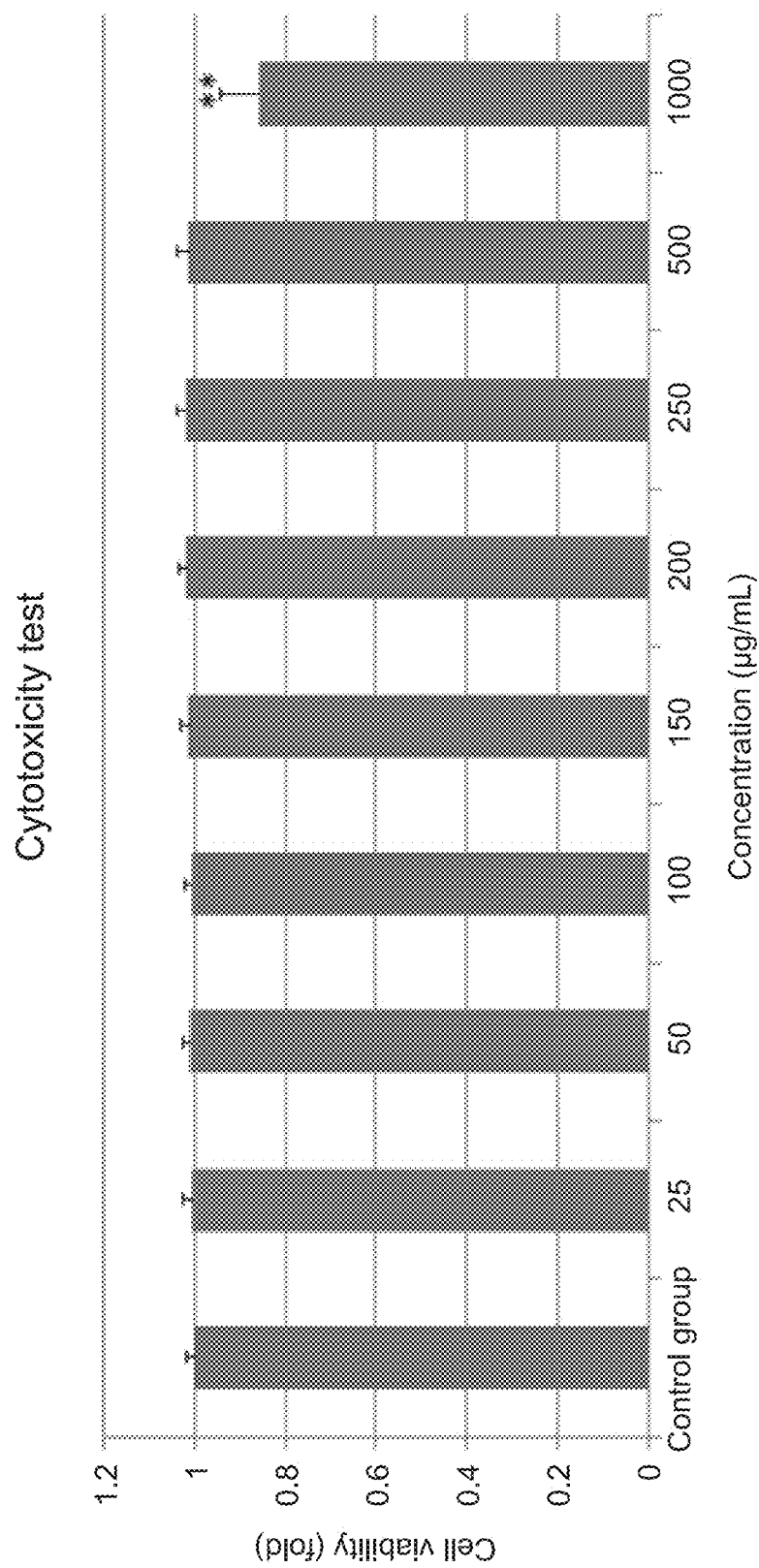
FIG. 1 shows the result of the cytotoxicity test for the ramie extract with different concentrations.

In the following detailed description, for purposes of explanation, numerous specific details are set forth in order to provide a thorough understanding of the disclosed embodiments. According to the description, claims and the drawings disclosed in the specification, one skilled in the art may easily understand the concepts and features of the present invention. The following embodiments further illustrate various aspects of the present invention, but are not meant to limit the scope of the present invention.

Ramie root is the root of *Boehmeria nivea* (L.) Gaud (also referred as ramie). In the traditional Chinese medicine, the ramie root has the effect on hemostasis, tocolysis, detoxification, and the like. The ramie root mainly comprises polyphenols and flavonoids, such as p-coumaric acid, caffeic acid, chlorogenic acid, hyperoside, and rutin.

The following briefly describes the extraction procedure for the ramie extract of the present disclosure. Firstly, the raw material of the ramie root is crushed, soaked in water, and extracted at 60° C. with water for 12 hours three times. Then, the resultant is sequentially concentrated 10 times, filtered, spray dried, mixed, powdered, filtered, and packaged, thereby obtaining the ramie extract. In one embodiment of the present disclosure, the ramie extract comprises p-coumaric acid and caffeic acid, and the ramie extract is stored in refrigerated and dry environment and prepared to a solution with water when using. In another embodiment of present disclosure, the ramie extract essentially comprises p-coumaric acid and caffeic acid. In other embodiments of the present disclosure, in addition to p-coumaric acid and caffeic acid, the ramie extract further comprises polyphenols and flavonoids comprising chlorogenic acid, hyperoside, rutin, and the like.

In one embodiment of the present disclosure, the weight ratio of p-coumaric acid to caffeic acid is 15:1 to 25:1, but is not limited thereto. In other embodiments of the present disclosure, the weight ratio of p-coumaric acid to caffeic acid is 10:1 to 30:1. In further embodiments of the present disclosure, the weight ratio of p-coumaric acid to caffeic acid is 19:1 to 21:1.

In one embodiment of the present disclosure, when the ramie extract with a concentration of 50 μg/mL to 700 μg/mL is provided to cells, the ramie extract entering into the cells can protect and repair the inner membranes of mitochondria to increase the activity thereof. In this way, the efficiency of the oxidative phosphorylation in mitochondrial inner membrane for ATP production is improved. In detail, the amount of ATP synthesized by the oxidative phosphorylation in mitochondria treated with the ramie extract is increased, the basal respiration of mitochondria is increased, the proton leakage of the mitochondrial inner membrane is decreased, the maximal respiratory capacity of mitochondria is increased, the spare respiratory capacity of mitochondria is increased, and the ATP coupling efficiency of mitochondria is increased. In one preferred embodiment of the present disclosure, the concentration of the ramie extract may be 100 μg/mL to 650 μg/mL. In one more preferred embodiment of the present disclosure, the concentration of the ramie extract may be 180 μg/mL to 520 μg/mL. In one further preferred embodiment of the present disclosure, the concentration of the ramie extract may be 200 μg/mL to 500 μg/mL.

In another embodiment of the present disclosure, when the ramie extract with a concentration of 50 μg/mL to 700 μg/mL is provided to cells, the ramie extract entering into the cells can increase the activity of telomerase. In this way, the telomerase with increased activity can repair telomeres so as to reduce the speed of the loss of telomeres. In one preferred embodiment of the present disclosure, the concentration of the ramie extract may be 100 μg/mL to 650 μg/mL. In one more preferred embodiment of the present disclosure, the concentration of the ramie extract may be 180 μg/mL to 520 μg/mL. In one further preferred embodiment of the present disclosure, the concentration of the ramie extract may be 250 μg/mL to 500 μg/mL.

Therefore, the activity of mitochondria and the activity of telomerase can be increased by providing the ramie extract to cells to achieve the effect of anti-aging.

As a manner for providing the ramie extract to cells, for example, the ramie extract may be taken in by oral administration. When the ramie extract is provided by oral administration, the effective dose of the ramie extract may be from 2.162 g to 5.406 g. The effective dose in human is obtained according to a conversion equation. The conversion equation is: (effective dose in human)=(effective dose in cell experiment)× (body weight of mice)× (conversion coefficient)× (body weight of human). The conversion coefficient is obtained from the conversion coefficient table. For example, when the body weight of mice is 20 g and the body weight of human is 60 kg, the conversion coefficient is 9.01.

To make the oral administration more convenient, the ramie extract is able to be made into a processed food, and the processed food is able to be provided in liquid form, solid form, powder form, granular form, paste form or colloidal form. In some embodiments of the present disclosure, without affecting the effect and the purpose of the present disclosure, the processed food of the ramie extract may also comprise other ingredients or additives, such as a carrier, a diluent, an adjuvant, an excipient, or a flavor enhancer. The excipient may make the formulation convenient and practical, and the flavor may improve the flavor of the formulation.

For example, the excipient may be starch, such as wheat starch, rice starch, corn starch, potato starch, dextrin, cyclodextrin, and the like; crystalline cellulose; saccharide, such as lactose, glucose, sugar, reduced maltose, cerealose, oligofructose, galactooligosaccharide, and the like; or glycitol, such as sorbitol, erythritol, xylitol, lactitol, mannitol, and the like.

For example, the flavor enhancer may be fruit extract, such as longan extract, lychee extract, grapefruit extract, and the like; fruit juice, such as apple juice, orange juice, lemon juice, and the like; essence, such as peach essence, plum essence, yogurt essence, and the like; sweetener, such as acesulfame potassium, sucralose, erythritol, oligosaccharide, mannose, xylitol, isomerized sugar, and the like; acid flavoring, such as citric acid, malic acid, tartaric acid, gluconate, and the like; or tea ingredient, such as green tea, oolong tea, *banaba* tea, *eucommia* tea, tieguanyin tea, *coix* tea, jiaogulan tea, *zizania latifolia* tea, kelp tea, and the like.

Moreover, the composition of the ramie extract according to the present disclosure may be a pharmaceutical or non-pharmaceutical composition and may also be health supplement. The ramie extract or the composition comprising the ramie extract may be encapsulated in a capsule for convenient oral administration. The ramie extract or the composition comprising the ramie extract may be encapsulated in a hard capsule in a dried powder form. Also, the ramie extract or the composition comprising the ramie extract may be encapsulated in a soft capsule in a liquid form, suspension form, paste form, powder form, or granular form.

The oil in the soft capsule for dissolving the ramie extract may be, for example, avocado oil, almond oil, flaxseed oil, fennel oil, *Perilla frutescens* oil, olive oil, olive squalene, sweet orange oil, orange roughy oil, sesame oil, garlic oil, cocoa butter, pumpkin seed oil, chamomile oil, carrot oil, cucumber oil, tallow fatty acid, kukui nut oil, lingonberry seed oil, brown rice germ oil, rice bran oil, wheat germ oil, safflower oil, shea butter, liquid shea butter, *perilla* oil, soybean oil, evening primrose oil, *camellia* oil, corn oil, rapeseed oil, saw palmetto extract oil, *coix* oil, peach kernel oil, celery seed oil, castor oil, sunflower oil, grapeseed oil, borage oil, macadamia nut oil, meadowfoam oil, cottonseed oil, peanut oil, turtle oil, mink oil, egg yolk oil, fish oil, palm oil, palm-kernel oil, wood wax oil, coconut oil, long-chain/medium-chain/short-chain triglyceride, diglyceride, butter, lard, squalene, squalane and pristane and hydrides thereof. In addition, both borage oil and evening primrose oil contain a great amount of gamma-linolenic acid which is an essential fatty acid for human body. Gamma-linolenic acid is favorable for retaining skin moisture, stimulating cell regeneration and increasing the activity of brown fat to burn fat.

In addition, several food additives approved for use, such as colorant, preservative, tackifier, binder, disintegrant, dispersant, stabilizer, gelatinizer, antioxidant, surfactant, preservative, and pH control agent, may be added to the processed food of the ramie extract.

The following demonstrates the effect of increasing the activity of mitochondria using the pharmaceutical or non-pharmaceutical composition of the present disclosure.

Example 1 is a ramie extract solution of 200 μg/mL, Example 2 is a ramie extract solution of 250 μg/mL, and Example 3 is a ramie extract solution of 500 μg/mL.

The following experiment is conducted by using skeletal muscle cells (C2C12). The C2C12 cells are cultured in DMEM with 10% fetal bovine serum (FBS). The cell subculture is described as follows. First, the cells are cultured to a certain amount, and then the culture medium is removed. The cells are rinsed with phosphate buffered saline (PBS) twice. Then, trypsin is added to react with the cells at 37° C. for 5 minutes, and then the culture medium is added to stop the reaction of trypsin. Then, the mixture is centrifuged at 300 g for 5 minutes to remove the supernatant and resuspended with the culture medium. Finally, the cell count in 175 T flask is $1 \times 10^6$ cells.

First, the cytotoxicity test for the ramie extract is conducted. Alamar blue is a cell viability assay reagent. In the Alamar blue cell viability assay kit, resazurin is a redox indicator, which is a nontoxic, cell-permeable, weakly fluorescent, and deep blue dye. Upon entering living, resazurin is reduced to resorufin, a compound that is pink and highly fluorescent, due to the reducing environment in the living cells. The cell viability may be evaluated by detecting the absorbance or fluorescence of resorufin. The higher absorbance or fluorescence of resorufin indicates the higher cell viability. High viability means healthy cells and a high proliferation ability. When the cells have a high proliferation ability, the amount of cells increases. Therefore, Alamar blue may be used as an indicator of cytotoxicity to reflect cell viability and cell proliferation.

The procedure for the cytotoxicity test of the ramie extract is described as follows. On the first day, the cells are cultured in a 96-well plate with a total volume of 200 μL and 10000 cells per well for one day. On the second day, the ramie extract is added, and the concentrations of the ramie extract in each well are 25, 50, 100, 150, 200, 250, 500, and 1000 μg/mL. The cells are incubated at 37° C. for one day. The ramie extract used here comprises p-coumaric acid and caffeic acid, and the weight ratio of p-coumaric acid to caffeic acid is 20.9:1. On the third day, the cytotoxicity test is conducted with Alamar blue. In detail, Alamar blue is prepared to a solution of 10 wt % in a dark environment, added to the 96-well plate with 100 μL per well, and incubated with the cells at 37° C. for 3 to 4 hours. Then, the absorbance and fluorescence are measured by ELISA reader (OD530/590), and the cell viability after being treated with the ramie extract is obtained to represent the cytotoxicity of the ramie extract.

The result of the cytotoxicity test for the ramie extract with different concentrations is shown as follows.

Referring to FIG. 1, FIG. 1 shows the result of the cytotoxicity test for the ramie extract with different concentrations. The control group is the cells not treated with the ramie extract, the vertical axis is the cell viability relative to the control group, and the symbol "**" ($P<0.01$) means significantly different relative to the control group.

In the cytotoxicity test of the ramie extract, as shown in FIG. 1, only the ramie extract of 1000 μg/mL causes a decrease in cell viability, while the ramie extracts less than 500 μg/mL have no effect on cell viability. This indicates that the ramie extracts less than 500 μg/mL have no cytotoxicity. Accordingly, 200, 250, and 500 μg/mL of the ramie extract are selected as Examples 1 to 3 of the present disclosure for the subsequent experiments.

Next, the experiment of increasing the activity of mitochondria by the ramie extract is conducted. In the experiment, tert-butyl hydroperoxide (t-BHP) is used as a substance that induces cellular oxidative stress damage and aging and inhibits the activity of mitochondria.

The experimental procedure for increasing the activity of mitochondria by the ramie extract is described in detail as follows. On the first day, the cells with culture medium are cultured in a 24-well plate for Seahorse XF analysis with a total volume of 100 μL and 25000 cells per well for 4 hours, and then 150 μL of culture medium is added and incubated for one day. On the second day, the ramie extract is added, and the concentrations of the ramie extract in each well are 200, 250, and 500 μg/mL with a total volume of the solution of 250 μL in each well. The cells are incubated with the ramie extract for one day. On the third day, 100 μM of t-BHP is added to each well and reacted with the cells for 1 hour, and then the culture medium in the well is replaced with 675 μL of the medium for measuring, a DMEM medium without FBS, and incubated in an incubator without $CO_2$ for 1 hour. Then, the oxygen consumption of cells in the well is measured by a Seahorse XF analyzer.

The measurement principle and procedure of Seahorse XF analyzer are described as follows. First, the basal respiration of cells is measured. Then, a ATP synthesis inhibitor is added to inhibit mitochondria to synthesize ATP, and the reduction of the oxygen consumption is equal to the oxygen consumption for ATP production. Then, an anti-coupler in a proper concentration, which causes no damage to the electron transport chain in the inner mitochondrial membrane, is added to evaluate the maximal respiration of the mitochondria. Finally, an electron transport chain inhibitor is added to totally stop the respiration in the mitochondria, and the background is measured, which is equal to the non-mitochondrial respiration. The oxygen consumption of the basal respiration of mitochondria is equal to the oxygen consumption of the basal respiration of cells minus the oxygen consumption of the non-mitochondrial respiration. The oxygen consumption for overcoming proton leakage is equal to the oxygen consumption of the basal respiration of mitochondria minus the oxygen consumption of mitochondria for ATP production. The oxygen consumption of the spare respiration is equal to the oxygen consumption of the maximal respiration minus the oxygen consumption of the basal respiration of mitochondria. The ATP coupling efficiency is equal to the oxygen consumption of mitochondria for ATP production divided by the oxygen consumption of the basal respiration of mitochondria.

Bioenergetic health index (BHI) is an index for evaluating the energy metabolism of mitochondria. BHI is calculated by the energy metabolism data of mitochondria as parameters, and the energy metabolism data of mitochondria are obtained by using Seahorse XF analyzer. BHI=[(the oxygen consumption of mitochondria for ATP production)× (the oxygen consumption of the spare respiration)]/[(the oxygen consumption for overcoming proton leakage)× (the oxygen consumption of the non-mitochondrial respiration)]. The higher BHI of cells means the better function of mitochondria in the cells, and the cells with better function are usually younger cells. Therefore, BHI may also be used as an indicator to evaluate the degree of aging.

The experimental results of increasing the activity of mitochondria by using the pharmaceutical or non-pharmaceutical composition of the ramie extract of the present disclosure are described as follows.

Figure 2:
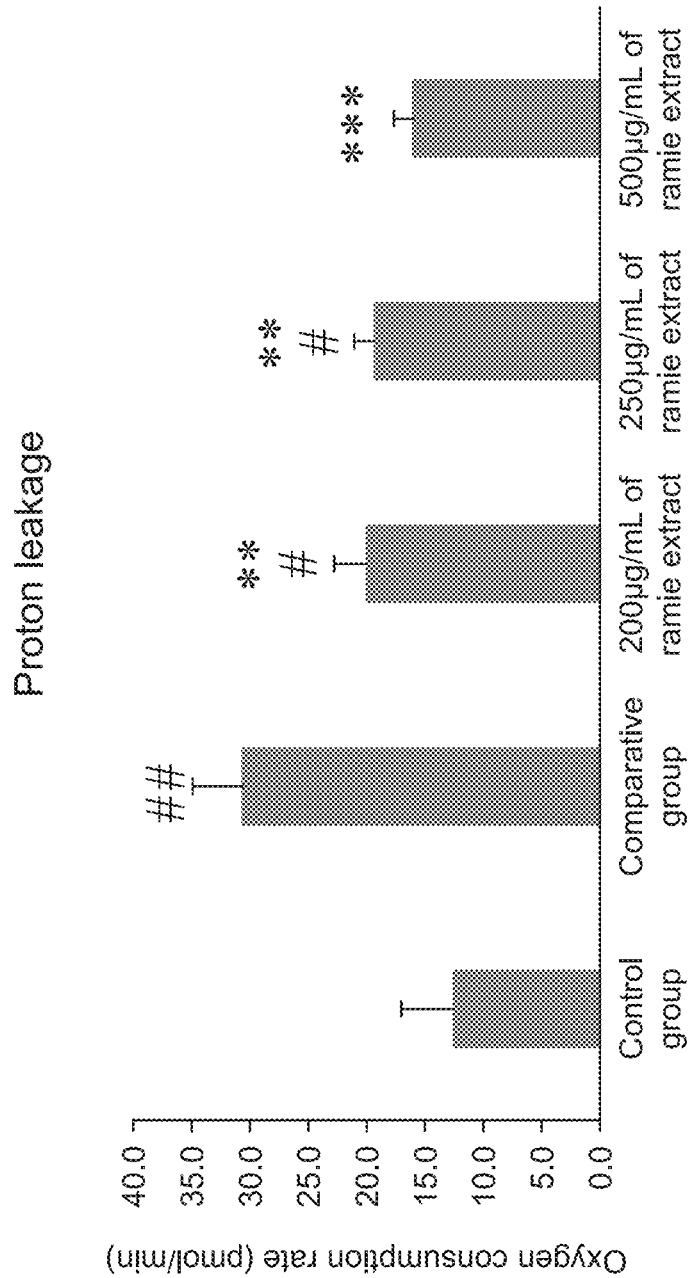
FIG. 2 shows the oxygen consumption of mitochondria for overcoming proton leakage.
Figure 3:
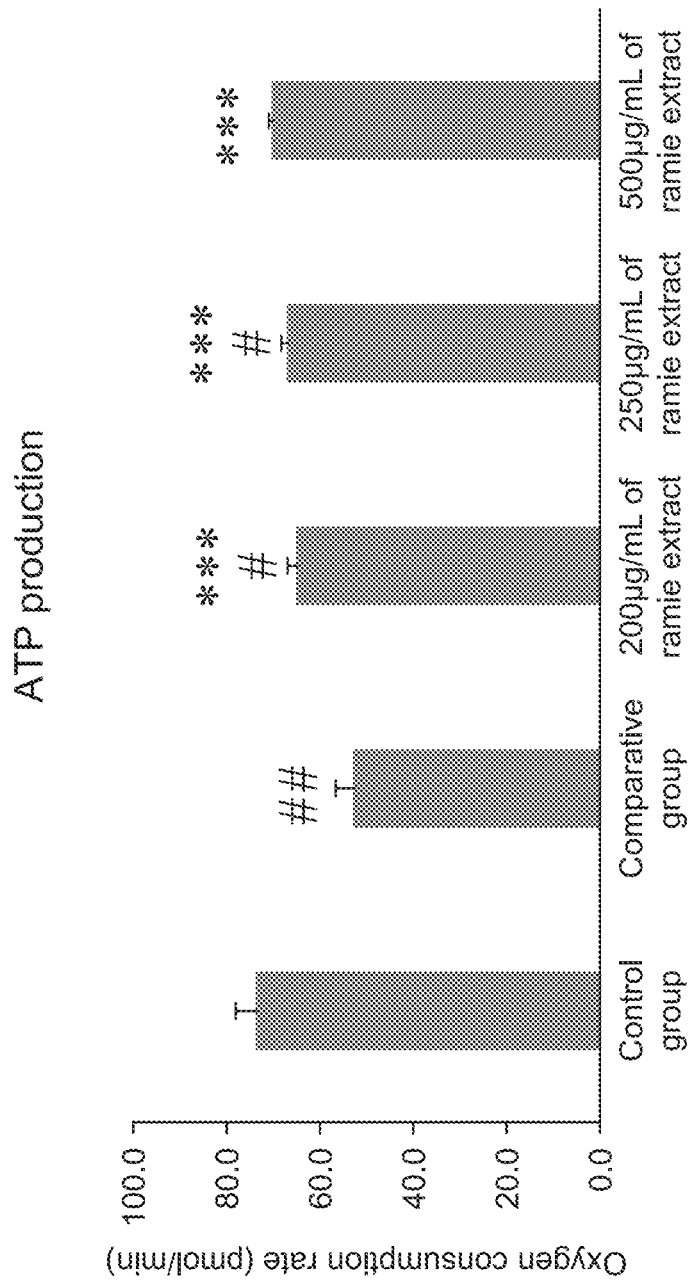
FIG. 3 shows the oxygen consumption of mitochondria for ATP production.
Figure 4:
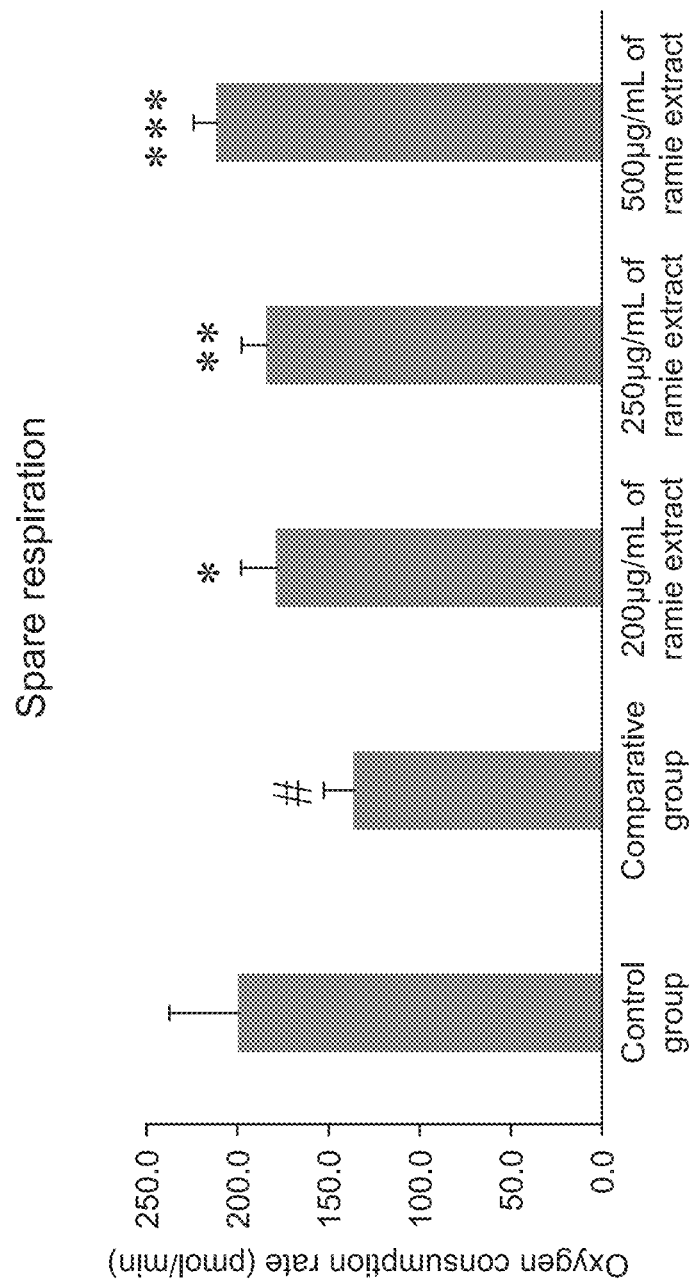
FIG. 4 shows the oxygen consumption of mitochondria for the spare respiration.
Figure 5:
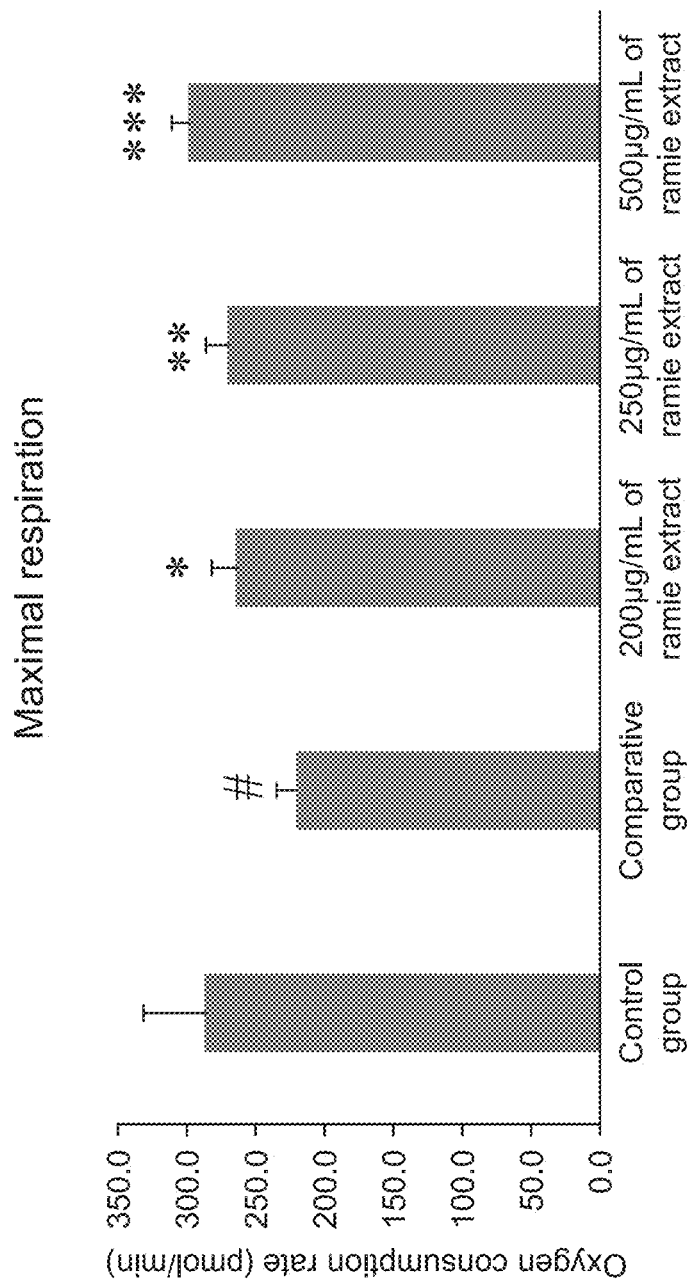
FIG. 5 shows the oxygen consumption of mitochondria for the maximal respiration.
Figure 6:
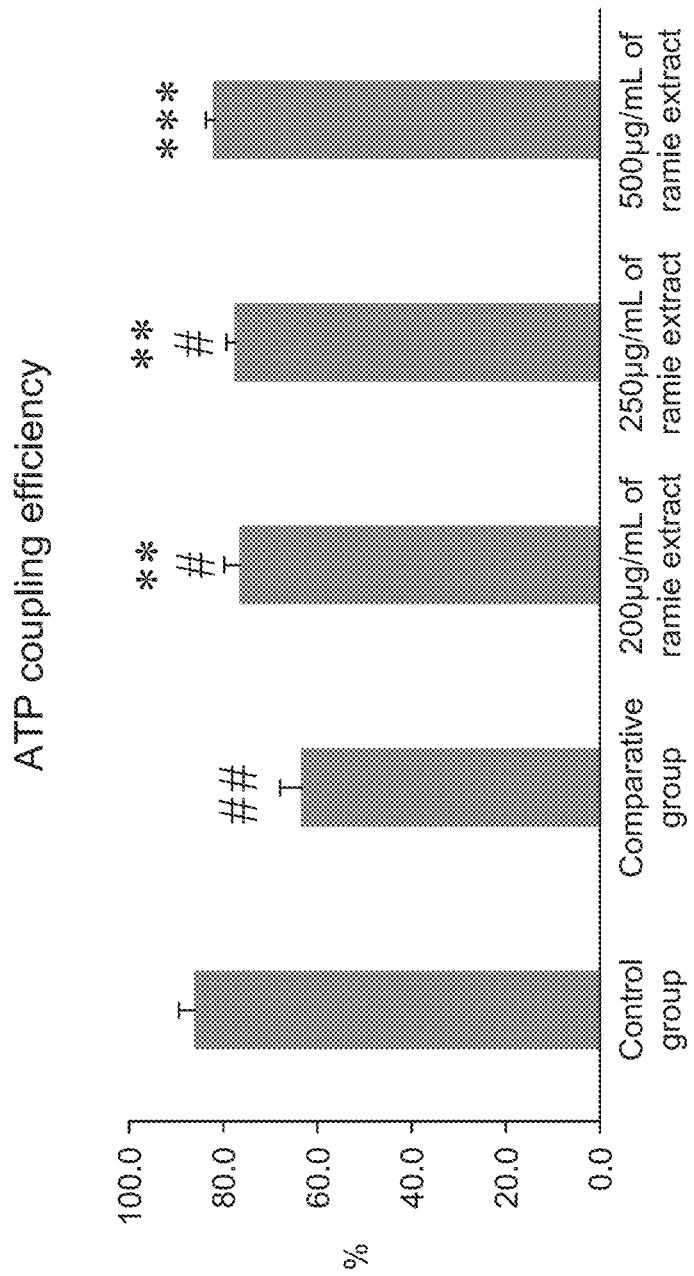
FIG. 6 shows the oxygen consumption of mitochondria for the ATP coupling efficiency.

Referring to FIGS. 2 to 6 and Table 1, FIG. 2 shows the oxygen consumption of mitochondria for overcoming proton leakage, FIG. 3 shows the oxygen consumption of mitochondria for ATP production, FIG. 4 shows the oxygen consumption of mitochondria for the spare respiration, FIG. 5 shows the oxygen consumption of mitochondria for the maximal respiration, FIG. 6 shows the oxygen consumption of mitochondria for the ATP coupling efficiency, and Table 1 shows the experimental data of each experiment. In FIGS. 2 to 5, the vertical axis is the oxygen consumption in pmol per minute. In FIG. 6, the vertical axis is the ATP coupling efficiency in percentage (%). The control group (Con.) is the cells not treated with t-BHP and the ramie extract, the comparative group (Comp.) is the damaged cells treated with 100 μM of t-BHP, and the experimental groups (Ex.) 1 to 3 are the cells treated with 200, 250, and 500 μg/mL of Examples 1 to 3, respectively, and then treated with 100 μM of t-BHP. Symbols "#" (P<0.05) and "##" (P<0.01) mean significantly different relative to the control group, and symbols "*" (P<0.05), "" (P<0.01), and "*" (P<0.001) mean significantly different relative to the comparative group.

TABLE 1

| Group | Ramie extract (μg/mL) | Oxygen consumption (pmole/min) | | | | ATP coupling efficiency (%) | BHI |
|---|---|---|---|---|---|---|---|
| | | Proton leakage | ATP production | Spare respiration | Maximal respiration | | |
| Con. | — | 12.53 | 73.78 | 200.25 | 286.57 | 85 | 2.03 |
| Comp. | — | 30.76 | 53.13 | 136.7 | 220.58 | 63 | 1.17 |
| Ex. 1 | 200 | 20.07 | 65.33 | 178.59 | 263.99 | 76 | 1.6 |
| Ex. 2 | 250 | 19.34 | 67.08 | 184.05 | 270.47 | 77 | 1.68 |
| Ex. 3 | 500 | 15.91 | 70.31 | 212.12 | 298.34 | 81 | 1.84 |

In the experiment of increasing the activity of mitochondria by using the pharmaceutical or non-pharmaceutical composition of the ramie extract, the function and activity of mitochondria are determined by the oxygen consumption of mitochondria. As shown in FIG. 2, in terms of the oxygen consumption of mitochondria for overcoming proton leakage, the comparative group is higher than the control group, and the experimental groups treated with the ramie extract of Examples 1 to 3 are less than the comparative group and close to the control group. As shown in FIG. 3, in terms of the oxygen consumption of mitochondria for ATP production, the comparative group is less than the control group, and the experimental groups treated with the ramie extract of Examples 1 to 3 are higher than the comparative group and close to the control group. As shown in FIG. 4, in terms of the oxygen consumption of mitochondria for the spare respiration, the comparative group is less than the control group, and the experimental groups treated with the ramie extract of Examples 1 to 3 are higher than the comparative group and close to the control group. As shown in FIG. 5, in terms of the oxygen consumption of mitochondria for the maximal respiration, the comparative group is less than the control group, and the experimental groups treated with the ramie extract of Examples 1 to 3 are higher than the comparative group and close to the control group. As shown in FIG. 6, in terms of the ATP coupling efficiency, the comparative group is less than the control group, and the experimental groups treated with the ramie extract of Examples 1 to 3 are higher than the comparative group and close to the control group. As shown in Table 1, in terms of BHI, the comparative group is less than the control group, and the experimental groups treated with the ramie extract of Examples 1 to 3 are higher than the comparative group and close to the control group.

According to the above experimental results, in the comparative group, the inner membrane of mitochondria is damaged so that more oxygen is needed to overcome the proton leakage, and the ATP production of the mitochondria, the spare respiratory capacity of mitochondria, the maximal respiratory capacity of the mitochondria, and the ATP coupling efficiency of the mitochondria are all decreased. Compared to the comparative group, the activity of mitochondria treated with the ramie extract of Examples 1 to 3 is increased by the ramie extract. This means that the ramie extract is able to protect and repair mitochondria under oxidative stress so that the inner membrane of mitochondria is less damaged. Less damage in the inner membrane means that mitochondria need less oxygen to overcome proton leakage so that the proportion of the oxygen consumption for ATP production in the oxygen consumption for the basal respiration is increased. In this way, the ATP production is increased, and the ATP coupling efficiency is also increased. The maximal respiratory capacity of the mitochondria is the capacity of mitochondria to work at maximal efficiency under oxidative stress. Compared to the comparative group, the maximal respiratory capacity of mitochondria treated with the ramie extract of Examples 1 to 3 in the experimental group is increased and close to the maximal respiratory capacity of mitochondria of the control group. The difference value between the oxygen consumption for the maximal respiration and the oxygen consumption for basal respiration is the oxygen consumption for the spare respiration. Compared to the comparative group, the spare respiratory capacity of mitochondria treated with the ramie extract of Examples 1 to 3 in the experimental group is increased and close to the spare respiratory capacity of mitochondria of the control group. This means an increased capacity of mitochondria to cope with oxidative stress. The increase of BHI means the improvement of the overall anti-aging ability of mitochondria. In summary, in the cells treated with the ramie extract of the present disclosure, the ATP production, the spare respiratory capacity, and the maximal respiratory capacity of mitochondria are increased, and the ATP coupling efficiency and BHI are also increased.

The experimental procedure for increasing the activity of telomerase by the ramie extract is described in detail as follows. On the first day, the cells are cultured in a 6-well plate with 200000 cells per well for one day. On the second day, the ramie extract is added, and the concentrations of the ramie extract in each well are 250 and 500 μg/mL. The cells are incubated with the ramie extract at 37° C. for one day. On the third day, the RNA of the cells is harvested by using TeloTAGGG™ Telomerase PCR ELISA kit (Roche). The polymerase chain reaction (PCR) is conducted according to the instruction of TeloTAGGG™ Telomerase PCR ELISA kit (Roche), and the cDNA obtained by PCR is stored at 4° C. in a refrigerator. On the fourth day, the activity of telomerase is measured by using TeloTAGGG™ Telomerase PCR ELISA kit. In detail, first, the telomere sequence of TAGGG is amplified as a PCR product by PCR. Then, the PCR product is reacted with the antibody and the hybridized probe in TeloTAGGG™ Telomerase PCR ELISA kit and colored, and the absorbance is measured at 450 nm. The higher absorbance means more telomere sequence protected by telomerase and further means higher activity of telomerase.

The experimental results of increasing the activity of telomerase by using the pharmaceutical or non-pharmaceutical composition of the ramie extract of the present disclosure are described as follows.

Figure 7:
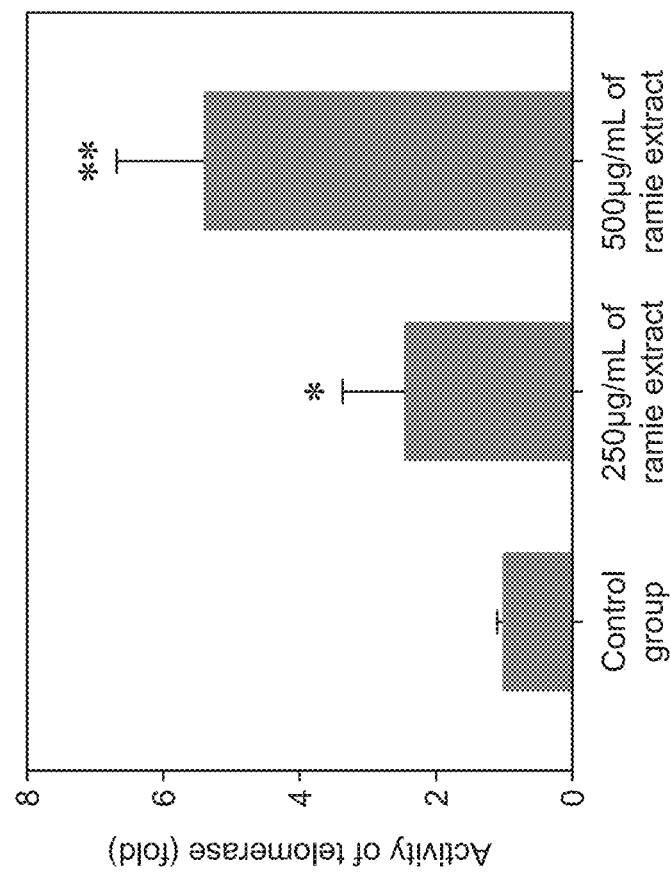
FIG. 7 shows the result of the activity test for the telomerase.

Referring to FIG. 7 and Table 2, FIG. 7 shows the result of the activity test for the telomerase. In FIG. 7, the vertical axis is the absorbance fold relative to the control group, which reflects the fold of the activity of telomerase relative to the control group. Symbol "*" (P<0.05) and symbol "**" (P<0.01) mean significantly different relative to the control group. The control group (Con.) is the cells not treated with the ramie extract, and the experimental groups (Ex.) 4 and 5 are the cells treated with 250 and 500 μg/mL of the ramie extract of Examples 2 and 3, respectively.

TABLE 2

|  | Ramie extract (μg/mL) | Activity of telomerase (fold) |
|---|---|---|
| Con. | — | 1 |
| Ex. 4 | 250 | 2.461 |
| Ex. 5 | 500 | 5.388 |

According to the above experimental results, compared to the control group, the activity of telomerase treated with the ramie extract of Examples 2 and 3 in the experimental group is increased. This means the ability of telomerase to repair telomeres is increased, thereby reducing the speed of the loss of telomeres.

In view of the above description, according to the present disclosure, referring to the use of ramie extract in preparing a composition for anti-aging, mitochondria are protected from oxidative stress to maintain their function and activity, including decrease in the proton leakage, increase in the ATP production, increase in the spare respiratory capacity, increase in the maximal respiratory capacity, increase in the ATP coupling efficiency, or increase in Bioenergetic Health Index (BHI), for the purpose of anti-aging. According to the present disclosure, referring to the use of ramie extract in preparing a composition for anti-aging, the activity of telomerase is also increased to repair telomere and reduce the speed of the loss of telomeres for the purpose of anti-aging.

What is claimed is:

1. A method of increasing telomerase activity in a subject in need thereof comprising administering to the subject an effective amount of a composition comprising ramie extract,
   wherein the ramie extract is from the root of *Boehmeria nivea* (L.) Gaud, and
   wherein the ramie extract is obtained by crushing the root of *Boehmeria nivea* (L.) Gaud, soaking in water, and extracting at 60° C. with water for 12 hours.

2. The method of claim 1, wherein the ramie extract comprises p-coumaric acid and caffeic acid.

3. The method of claim 2, wherein the weight ratio of p-coumaric acid to caffeic acid is 10:1 to 30:1.

4. The method of claim 1, where in the ramie extract is present in the composition at a concentration of 50 μg/mL to 700 μg/mL.

5. The method of claim 1, wherein the composition is a pharmaceutical composition.

* * * * *